United States Patent [19]

Schulbaum

[11] Patent Number: 4,969,596
[45] Date of Patent: Nov. 13, 1990

[54] INFECTIOUS WASTE DISPOSAL CONTAINER

[75] Inventor: Robert I. Schulbaum, E. Norwich, N.Y.

[73] Assignee: Biosystems Partners, Farmingdale, N.Y.

[21] Appl. No.: 383,913

[22] Filed: Jul. 21, 1989

[51] Int. Cl.$^5$ ............................................. B65D 43/14
[52] U.S. Cl. ............................... 229/125.42; 220/404; 229/138; 229/140; 229/149; 229/907
[58] Field of Search .................... 220/403, 404, 1 T; 229/125.42, 137, 138, 140, 143, 144, 149, 907

[56] References Cited

U.S. PATENT DOCUMENTS

| | | | |
|---|---|---|---|
| 2,292,653 | 8/1942 | Palmer | 229/138 |
| 2,797,041 | 6/1957 | Rondove | 229/140 |
| 3,365,114 | 1/1968 | Macchi | 229/140 |
| 3,549,080 | 12/1970 | Gill | 206/631.3 |
| 3,581,977 | 6/1971 | Kirsky | 229/138 |
| 3,684,155 | 8/1972 | Smith | 220/404 |
| 3,825,150 | 7/1974 | Taylor | 220/404 |
| 4,315,592 | 2/1982 | Smith | 229/907 |
| 4,497,433 | 2/1985 | Wischusen, III | 229/140 |
| 4,534,489 | 8/1985 | Bartlett | 229/907 |
| 4,535,928 | 8/1985 | Capo | 229/138 |
| 4,662,559 | 5/1987 | Uryu | 229/907 |
| 4,730,770 | 3/1988 | Walton | 229/125.42 |
| 4,811,849 | 3/1989 | Rausing | 229/125.42 |
| 4,863,052 | 9/1989 | Lambert | 229/907 |
| 4,892,223 | 1/1990 | Dement | 220/404 |

Primary Examiner—Gary E. Elkins
Attorney, Agent, or Firm—Brooks & Kushman

[57] ABSTRACT

A corrugated, lightweight, foldably collapsible container for storing infectious waste in first and second storage positions is disclosed. The container comprises a collapsible receptacle having a foldably sealed bottom portion and a plurality of side panels forming an upwardly opening receptacle for receiving and containing waste therein. The container further has a top portion integrally formed with the receptacle, the top portion being operable to foldably form a spout portion for receiving waste therethrough, and also operable to quickly and foldably close into a first storage position for temporary storage of its contents, and to foldably close into a second storage position to facilitate more permanent storage of the waste contained therein, and further to facilitate safe movement of the container. In a preferred embodiment the container also incorporates a leak-proof removable plastic bag acting as a liner to further provide additional protection against leaks of the contents of the container.

27 Claims, 7 Drawing Sheets

INFECTIOUS WASTE DISPOSAL CONTAINER

BACKGROUND OF THE INVENTION

1. Technical Field

This invention relates to foldably sealable container systems and, more particularly, to a corrugated, foldably sealable waste container for storing and transporting infectious waste products.

2. Background of the Invention

Foldably sealable containers are used in a variety of applications for holding a variety of products. When dealing with infectious waste products, however, such as those found in the medical industry, unique concerns and requirements arise. Containers suitable for holding and storing used surgical sponges, bandages, gauze and similar products which have come in contact with infectious agents all require disposal in a waste container suitable to safely and securely store such products. This concern is particularly acute at the present time where used surgical and hospital products which have been contaminated with diseased blood and blood by-products are involved.

To be more effective, it would also be helpful if a container suitable for storing infectious wastes and other like products was readily foldable to provide quick, temporary sealing of the container for short time periods, such as for overnight storage. This would further help reduce the chance of accidental human contact with the infectious waste products being held therein. It would further be helpful if such an infectious waste container were operable to fold into a more secure and permanent storage configuration to facilitate safer transportation of the container.

In using such a waste container as explained above, it would also be helpful if the container were made of a lightweight material. To further help facilitate safe disposal of infected waste products, it would be desirable for such a container to be inexpensive, lightweight, relatively easy to manufacture, and structurally strong, such as a corrugated-type container. An inexpensive, lightweight, corrugated container would simplify disposal of infectious waste products because the container itself could be disposed of along with the waste products.

Another desirable feature of such a container would be an opening which facilitates the entry of waste products and yet partially seals the container. This would further help prevent accidental and unintended human contact with the contents of the container.

Still another desirable feature would be the ability of such a container to collapse into a flat or compact structure suitable for easy transportation and storage before the container is put to use.

In view of the foregoing, it is an object of the present invention to provide an infectious waste container having a spout-like opening operable to help facilitate placement of infectious waste products inside the container and to partially restrict access to the container to thereby help prevent accidental human contact with its contents.

It is a further object of the present invention to provide an infectious waste disposable container capable of being foldably sealed in a first storage position for quick, temporary storage of its contents, such as for overnight storage, to help reduce the chance of accidental human contact with its contents.

It is yet another object of the present invention to provide an infectious waste disposal container capable of being foldably collapsed into a second storage position for more secure storage of its contents and more secure and safe transportation of the container.

It is still another object of the present invention to provide a corrugated container that is lightweight, easily manufactured and relatively inexpensive, and which may readily be disposed of along with its contents.

It is a further object of the present invention to provide an infectious waste disposal container which may be foldably collapsed to form a compact structure suitable for easy and space-saving transport and storage until it is needed.

SUMMARY OF THE INVENTION

The present invention overcomes the limitations of prior art waste disposal containers by providing a foldably collapsible container for storing waste in first and second storage positions. The container comprises a foldably sealed bottom portion and a plurality of side panels which form an upwardly opening receptacle for receiving and containing waste therein. The container also comprises a top portion integrally formed with the receptacle means and side panels which is operable to foldably form a spout portion for receiving waste therethrough. The top portion is also operable to foldably close into the first storage position to thereby facilitate quick closure of the container, and to foldably close into the second storage position to facilitate more permanent storage of the waste therein and safe movement of the container. The container may also incorporate a removable, leak-proof liner, such as a leak-proof plastic bag, to reside within an interior area of the container for further enhancing secure storage of the waste within the container, and may also have its inner surfaces coated with a moisture resistant coating such as wax.

BRIEF DESCRIPTION OF THE DRAWINGS

The various advantages of the present invention will become apparent to one skilled in the art by reading the following specification and sub-joined claims and by referencing the following drawings in which:

DETAILED DESCRIPTION OF THE PREFERRED EMBODIMENT

Figure 1:
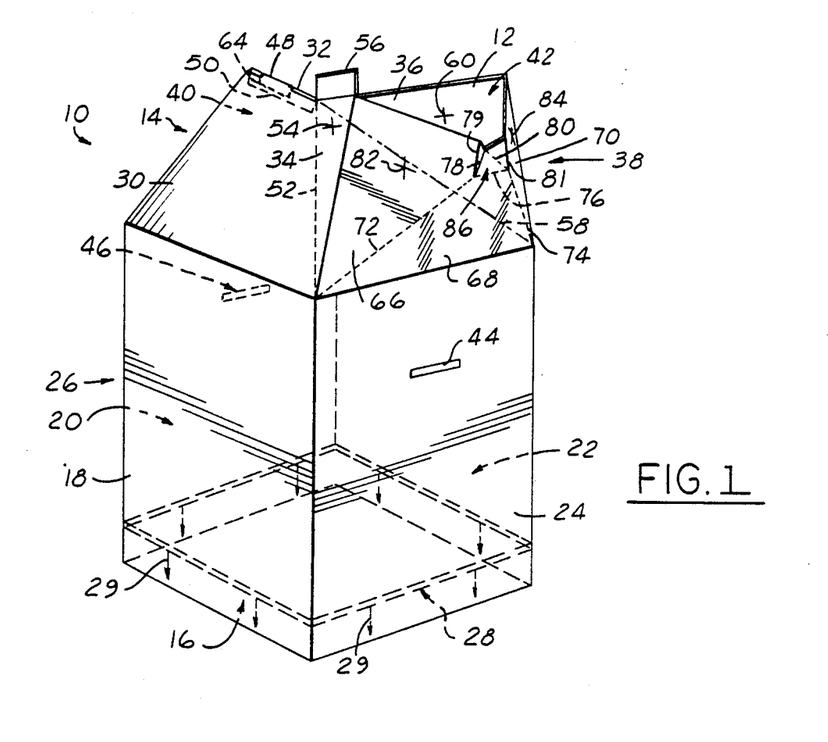
FIG. 1 is a perspective view of the container showing the top portion of the container configured in a spout-like opening for receiving infectious waste products therethrough.

Referring first to FIG. 1, there is shown an illustration of an infectious waste container 10. The container 10 is preferably constructed of corrugated material to provide structural rigidity, but may be constructed of a wide variety of materials to suit specific needs and requirements. The inside of the container preferably also is coated with a moisture resistant coating 12 such as wax, to improve its moisture resistant characteristics.

The container 10 generally comprises top and bottom portions 14 and 16 respectively, integrally formed with a plurality of vertical side panels 18, 20, 22 and 24 to form a receptacle means 26 in the shape of a box-like container. An optional, removable support member 28, which will also preferably be of a corrugated material, is also shown as indicated by dashed lines, and is adapted to rest against the bottom portion 16 of the container 10 to provide additional structural support to the container 10. The support member 28 has been shown in FIG. 1 as being elevated from the bottom portion 16 to more clearly show its placement within the container 10, although it should be understood that support member 28 will be resting flush against bottom portion 16 when the container 10 is in use (as indicated by the arrows 29).

The top portion 14 has foldable, collapsible first and second flap portions 30 and 32 which in turn have integral foldable portions 34 and 36 respectively, the functions of which will be explained shortly. Only a partial, view of first flap portion 32 can be seen in FIG. 1, although first flap portion 32 is shown clearly in subsequent views of the container 10 herein.

Top portion 14 also has first and second end portions 38 and 40, the first end portion 38 and portions 34 and 36 of the first and second flap portions 30 and 32 being operable to form a spout-like opening 42 for receiving waste therethrough. The first and second flap portions 30 and 32, foldable portions 34 and 36, and the first and second end portions 38 and 40 are integrally formed with the receptacle means 26 thereby forming a single piece, lightweight, integrally formed structure which is relatively easy and inexpensive to manufacture. (This is explained in more detail relative to FIG. 17 below). The inexpensiveness of the container 10 provides the added benefit of making it disposable along with its contents, thereby further enhancing its effectiveness in safely storing infectious wastes, since accidental human contact with its contents will be less likely to occur if the contents do not have to be removed therefrom for permanent disposal. It should be understood, however, that the container 10 may take a wide variety of forms and has been illustrated as a rectangular shaped container for purposes of illustration only.

The receptacle means 26 further comprises first and second slat-type cut-out sections 44 and 46 in side panels 24 and 20 respectively. The functions of the slat-type cut-outs 44 and 46 will be explained in detail shortly in connection with FIGS. 14–16.

The first flap portion 30 of the top portion 14 further includes a locking cut-out slot 48 within a first locking flap 50, the functions of which will also be explained shortly. Locking flap 50 has been illustrated with dashed lines to indicate its existence within the top portion 14, and would normally not be visible when the top portion 14 is foldably formed to provide spout-like opening 42. First flap portion 30 also contains score line 52 for facilitating easy folding of foldable portion 34; a slit-cut 54 formed by intersecting horizontal and vertical lines; and a second locking flap 56. The functions of slit-cut 54 and the second locking flap 56 will also be explained shortly.

The second flap portion 32 further comprises a score-line 58, which would also not normally be visible from the view provided in FIG. 1. As such, scoreline 58 has been illustrated in FIG. 1 as a series of short and long dashed lines so as not to be confused with other dashed lines representing areas of the container not normally visible from the view provided in FIG. 1. Second flap portion 32 also comprises a slit-cut 60 identical to slit-cut 54 for working cooperatively with slit-cut 54 to help hold an optional liner bag 62 (shown in FIG. 2) securely therein. Second flap portion 32 also includes a locking tab 64 which has also been partially illustrated by dashed lines to indicate its partially hidden existence, and which is adapted to extend through locking cut-out slot 48 to hold first and second flap portions 30 and 32 securely together when top portion 14 is formed into spout-like opening 42.

The first end portion 38 is comprised of side panels 66, 68 and 70 formed by scorelines 72, 74, 76, 78 and 80. Folding lines 79 and 81 have also been provided, and will be discussed in more detail along with scorelines 76, 78 and 80 shortly. Side panels 66 and 70 are further shown having slit-cuts 82 and 84 respectively for working cooperatively with slit-cuts 54 and 60 to further help hold liner bag 62 (shown in FIG. 2) securely in an open position along the periphery of spout-like opening 42. After the liner bag 62 is positioned within the container 10, the open top of the bag is folded up and over the edge lip of the opening 42 and portions of the bag are manually pushed (inserted) through the "X" shaped slit-cuts 54, 60, 82 and 84 which hold the bag firmly in position.

First end portion 38 further has a holding portion 86 which operates to hold first end portion 38 and portions 34 and 36 of first and second flap portions 30 and 32 in a spout-like opening. The operation of the holding portion 86 will also be discussed below in connection with the operation of the container 10.

Figure 2:
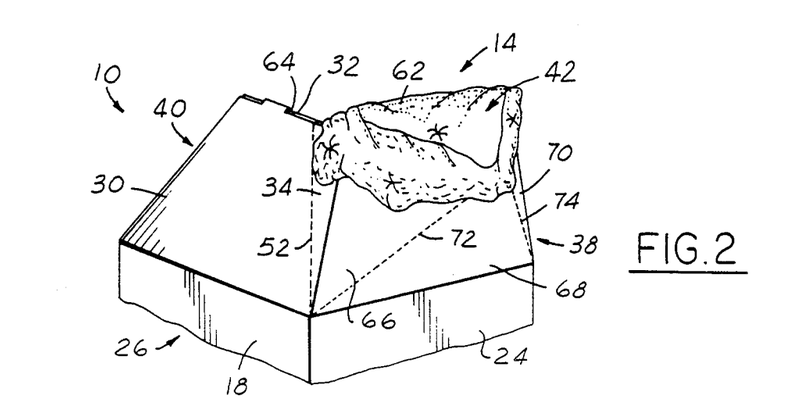
FIG. 2 is a perspective view of the top portion of the container showing a portion of the removable plastic liner bag inserted into the spout-like opening and folded outwardly over the edges of the spout-like opening, and tucked into the slit-type cuts of the top portion.

Turning now to FIG. 2, the configuration of the optional liner bag 62 is partially shown. The liner bag 62 may be made from any leak-proof material, but will preferably be of a plastic type of material to facilitate easy insertion of the bag 62 into the receptacle means 26 and easy folding to conform to spout-like opening 42. To hold the portion of liner bag 62 which protrudes through spout-like opening 42 in an open position, the portions of the liner bag 62 which overlay slit-cuts 54, 60, 82 and 84 are pushed through those slit-cuts, whereby slit-cuts 54, 60, 82 and 84 will operate to hold the liner bag 62 securely over and against portions 34 and 36 and side panels 66, 68 and 70 in an open position. When the container 10 is filled, portions of liner bag 62 being held by slit-cuts 54, 60, 82 and 84 may be removed therefrom and the bag 62 tied closed, thus allowing the container 10 to be sealed with the liner bag 62 enclosed completely therein.

Figure 3:
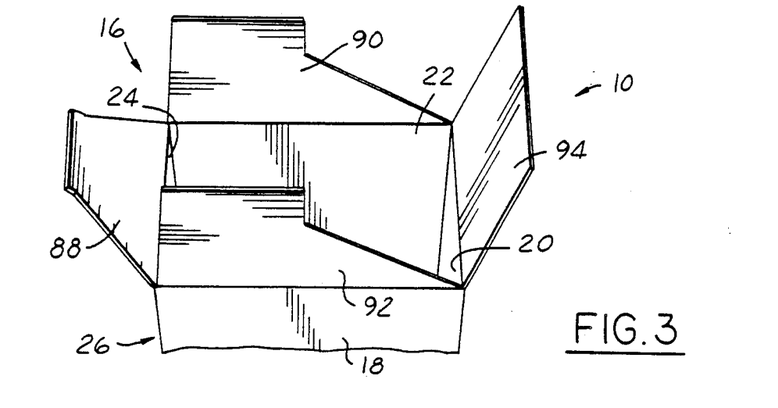
FIG. 3 is a perspective view of the bottom portion of the container showing the panels of the bottom portion in a fully open position ready to be foldably collapsed as a first step in assembling the container.

In FIG. 3, a bottom view of the container 10 is illustrated which shows its bottom portion 16 in an open position ready to be foldably collapsed as a first step in assembling the container 10. Bottom portion 16 is comprised of a first overlapping end flap 88, a pair of overlapping side flaps 90 and 92, and an end flap 94. As can be seen, each of the flaps 88, 90, 92 and 94 are integrally formed with vertical side panels 18, 20, 22 and 24, thus forming an integral part of the container 10.

Figure 4:
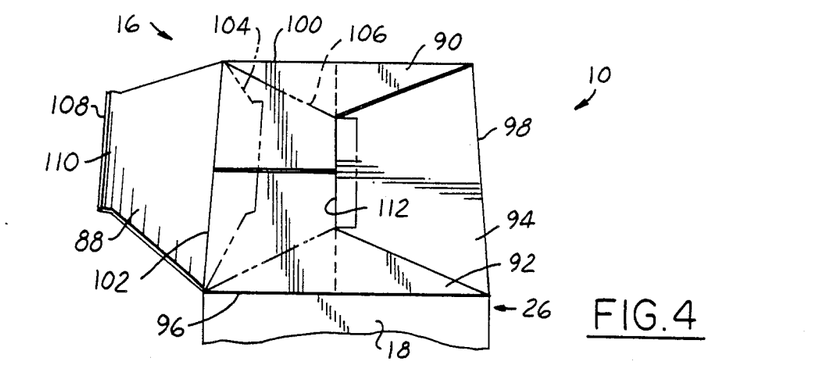
FIG. 4 is a perspective view of the bottom portion of the container showing more clearly how the panels of the bottom portion foldably collapse into a cooperatively locking arrangement.

In FIG. 4 the folding operation of the flaps 88, 90, 92 and 94 of the bottom portion 16 is illustrated as the bottom portion 16 is foldably collapsed into a secure locking arrangement. Initially, end flap 94 is folded downward relative to the receptacle means 26 to a position substantially parallel with longitudinal edges 96, 98, 100, and 102 of the side panels 18, 20, 22 and 24, and substantially orthogonal to the side panels 18, 20, 22 and 24. Next, overlapping side flaps 90 and 92 are foldably collapsed towards each other to lay partially flush over and against end flap 94. Overlapping end flap 88 is then articulated foldably downward, as illustrated by dashed lines 104 and 106, overlapping side flaps 90 and 92 and end flap 94 until it is also in abutting contact and flush against the side panels 90 and 92 and end panel 94. When overlapping end flap 88 is flush against the panels 90, 92 and 94, a slight downward force will be applied to it to force it inwardly until an edge 108 of its locking flap 110 clears an edge 112 of the end flap 94, and is thus disposed underneath end flap 94. At this point, when pressure is released on overlapping end flap 88, its locking flap 110 will be held securely underneath the edge 112 of end flap 94, thereby holding overlapping end flap 88 in a secure, locking fashion over panels 90 and 92 and underneath edge 112 of end flap 94. The bottom portion 16 as it appears in a final assembled position is shown more clearly in FIG. 5. As can be seen, overlapping end flap 88 now partially covers side flaps 90 and 92, and has its locking flap 110 securely held underneath end flap 94.

Figure 5:
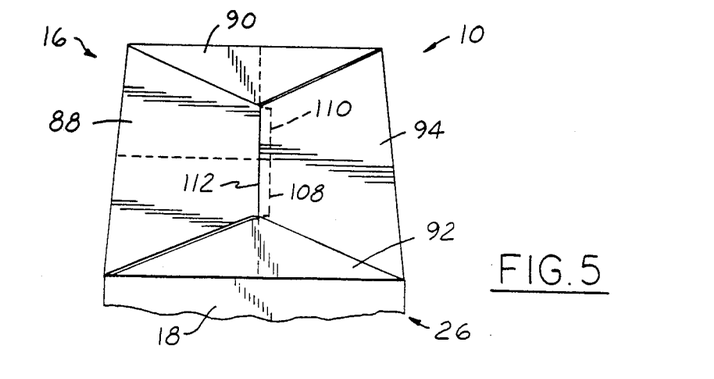
FIG. 5 is a perspective view of the bottom portion of the container showing the bottom portion in its final, assembled form.

Referring further to FIG. 5, to unfold the bottom portion 16 of the container 10, pressure may be applied in a downward fashion against end flap 94 and against overlapping end flap 88 until edge 112 of end flap 94 clears edge 108 of overlapping end flap 88 as both flaps 88 and 94 travel in a partial, downward, arcuate path. Overlapping end flap 88 may then first be lifted to an open position, with the overlapping side flaps 90 and 92 following next, and end flap 94 following last.

Figure 6:
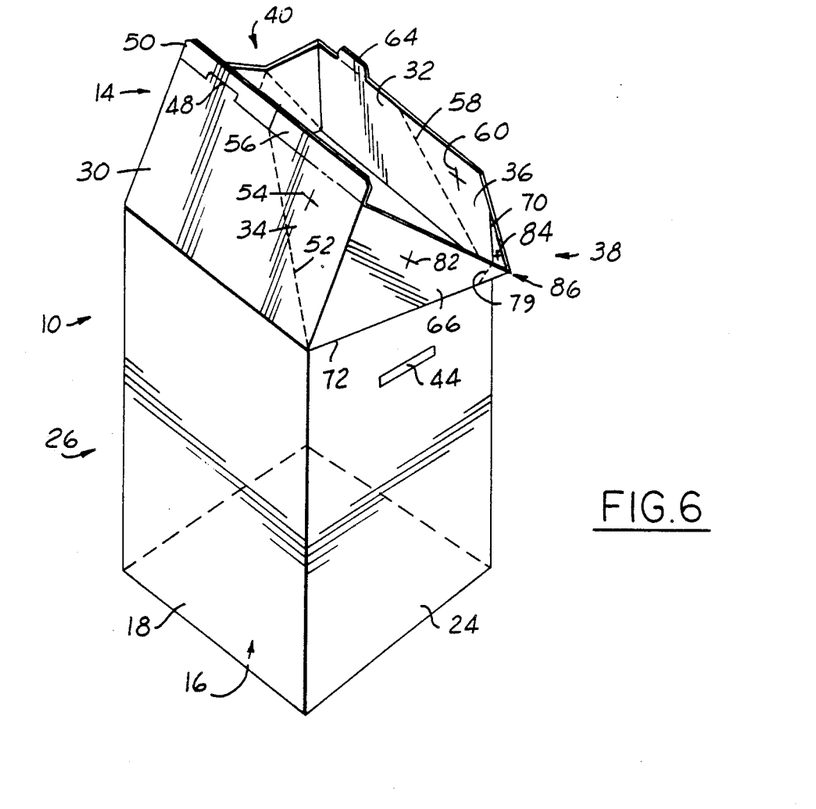
FIG. 6 is a perspective view of the container showing its top portion in a fully open position with the first and second end portions of the top portion protruding outwardly relative to each other, and ready for the first step in assembling the top portion into a spout-like opening.

Referring now to FIG. 6, the top portion 14 of the container 10 is shown in a fully open position ready to be either collapsed into first or second storage positions or formed into spout-like opening 42. As can be seen, first and second end portions 38 and 40 will be protruding foldably outwardly relative to the receptacle means 26, and will be pulling first and second flap portions 30 and 32 slightly towards each other. (For simplicity, the removable support member 28 has not been illustrated in FIG. 6).

Figure 7:
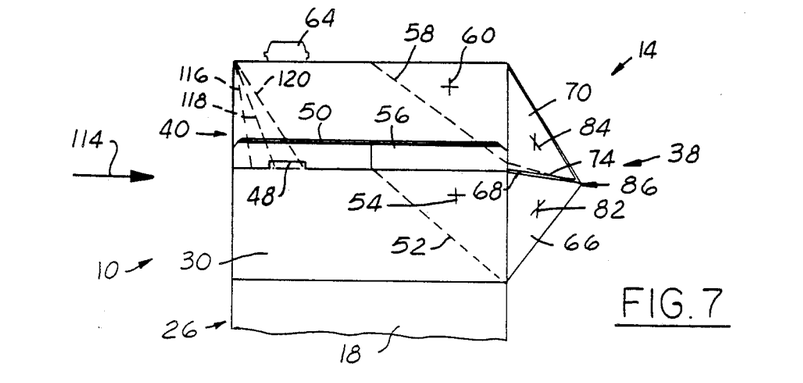
FIG. 7 is a perspective view of the container showing more clearly how the second end portion of the top portion is folded inwardly relative to the first end portion as a second step in assembling the top portion into a spout-like opening.
Figure 8:
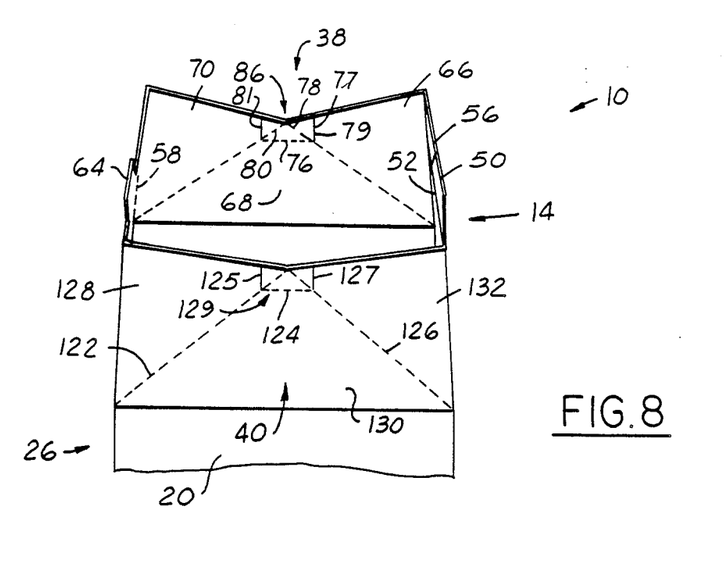
FIG. 8 is a perspective view of the container showing more clearly the score lines and folding lines of the first and second end portions which help facilitate the folding of the top portion into a spout-like opening.

In FIG. 7, the container 10 is shown as the first step in forming spout-like opening 42 out of top portion 14 is performed. The first step essentially consists of directing an inward force along directional arrow 114 until second end portion 40 is forced inwardly, as indicated by phantom lines 116, 118 and 120, into an inwardly resting position, as is generally shown in FIG. 7. While the second end portion 40 is being pushed inwardly, first locking flap 50 will also be folded downwardly inward into the container 10. Referring now to FIG. 8, the inward movement of the second end portion 40 is facilitated by score lines 122, 124 and 126, and folding lines 125 and 127, which define portions 128, 130 and 132 of the second end portion 40. Folding lines 125 and 127, score line 124 and the portions of score lines 122 and 126 within folding lines 125 and 127 and score line 124 further form a holding portion 129, the function of which will be described in detail shortly. The score lines 122, 124 and 126 form a small triangle residing within a larger triangle and operate to allow second end portion 40 to be foldably articulated into and remain resting in an inward fashion relative to first end portion 38.

Figure 9:
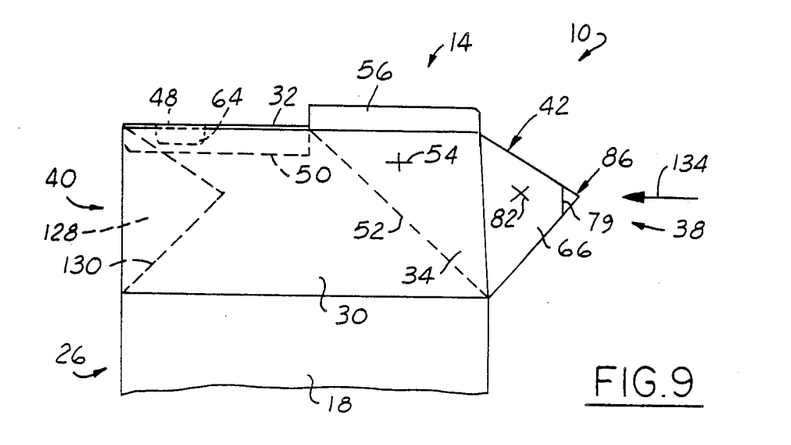
FIG. 9 is a side view of the container showing the direction of a force that is applied to the first end portion to push the first end portion inwardly to thereby form a spout-like opening.

The container 10 is shown in FIG. 9 after the first step in forming spout portion 42 has been performed. The first locking flap 50 has been foldably inserted partially between the undersurface of foldable portion 32 and the undersurface of portion 128, which is indicated in FIG. 9 by dashed lines. Locking tab element 64 is also shown by dashed lines as being foldably inserted through locking cut-out slot 48, also indicated by dashed lines, thereby holding first and second flap portions 30 and 32 in a secure, closed position.

Figure 10:
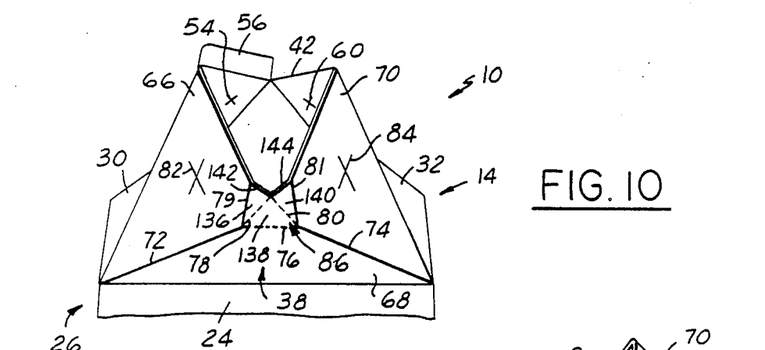
FIG. 10 is a perspective view of the top portion of the container showing more clearly the holding portion, the folding lines and score lines which enable the first end portion to be articulated into and remain resting in a spout-like opening.

The final step in forming spout-like opening 42 consists of applying an inward directional force along directional line 134 in FIG. 9 against holding portion 86. This causes holding portion 86 to fold inwardly with a snap-action like movement to an inwardly resting position as shown more clearly in FIG. 1. The snap-action like movement of the holding section 86 can best be described with reference to FIG. 10, wherein a direct, head-on view of the spout-like opening 42 is shown when the holding portion 86 has been pressed into an inward resting position. As can be seen in FIG. 10, the holding portion 86 is made up of three triangular portions 136, 138 and 140, which are formed by score lines 76, 78 and 80, and folding lines 79 and 81. The total distance provided by edges 142 and 144 of triangular sections 136 and 140 respectively is greater than the distance of score line 76 of triangular portion 138. As such, portions 136 and 140 will exert outward forces on side panels 66 and 70 as the triangular portions 136, 138 and 140 move inwardly towards a position of vertical, coplaner alignment. Once the triangular portions 136, 138 and 140 just pass a point of vertical coplanar alignment, the outward forces exerted by triangular portions 136 and 140 will force them and portion 138 inwardly with a snap-action like force.

Holding portion 86 serves to hold first end portion 38 in a more open position to help form the spout-like opening 42, and thereby help facilitate easy disposal of waste products through the spout-like opening 42 into the receptacle means 26.

Figures 11, 12:
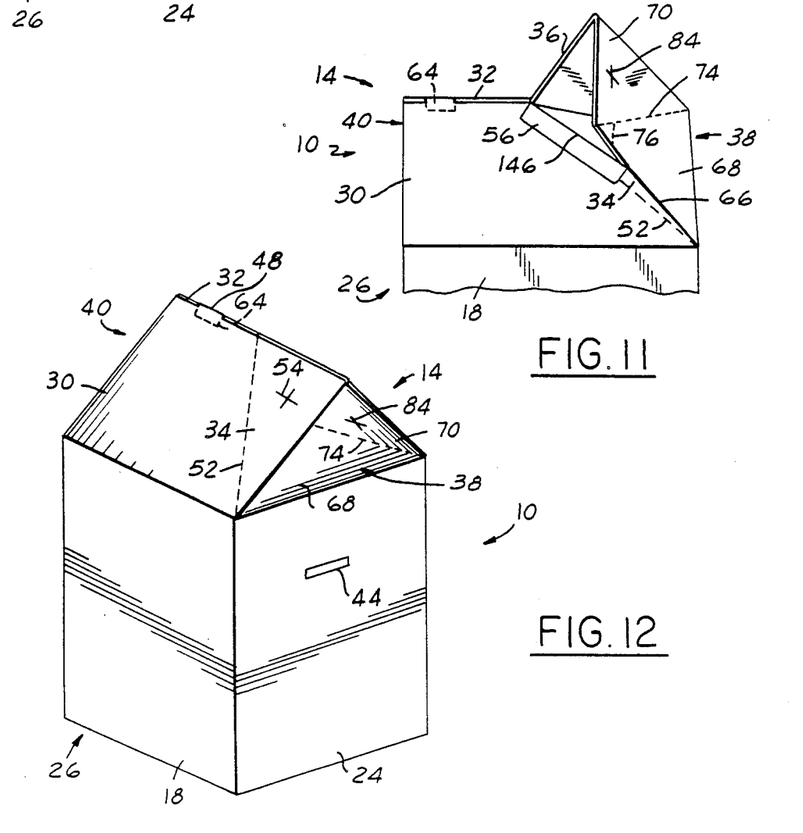
FIG. 11 is a perspective view of the container showing the first end portion in a partially collapsed state as a first step in forming a first storage position.
FIG. 12 is a perspective view of the container showing the top portion after it has been foldably articulated into the first storage position.

The container 10 is also foldably collapsible into first and second storage positions, and the process of foldably articulating first end portion 38 into the first storage position will now be described. Referring back to FIG. 9 momentarily, the first step in forming the first storage position consists of applying an inward force along directional line 134. The force is applied until the insides of portions 66 and 70 of first end portion 38 are pressing almost flush against the insides of foldable portions 34 and 36 respectively, as can be seen in FIG. 11. Once portions 66 and 70 are resting almost against portions 34 and 36, second locking flap 56 is folded inwardly relative to the receptacle means 26 along edge 146 until it is substantially orthogonal to portions 34 and 66. Portions 34 and 66 and portions 36 and 70 are then moved towards each other, whereby second locking flap 56 will become securely held between the insides of portions 36 and 70 when the connector 10 is in the first storage position. The container 10 as it appears in its first storage position is shown in FIG. 12. The first storage position allows quick sealing of the container 10 for temporary periods, such as for overnight storage, and helps prevent accidental human contact with the infectious waste products inside the container 10.

Figures 13, 14, 15:
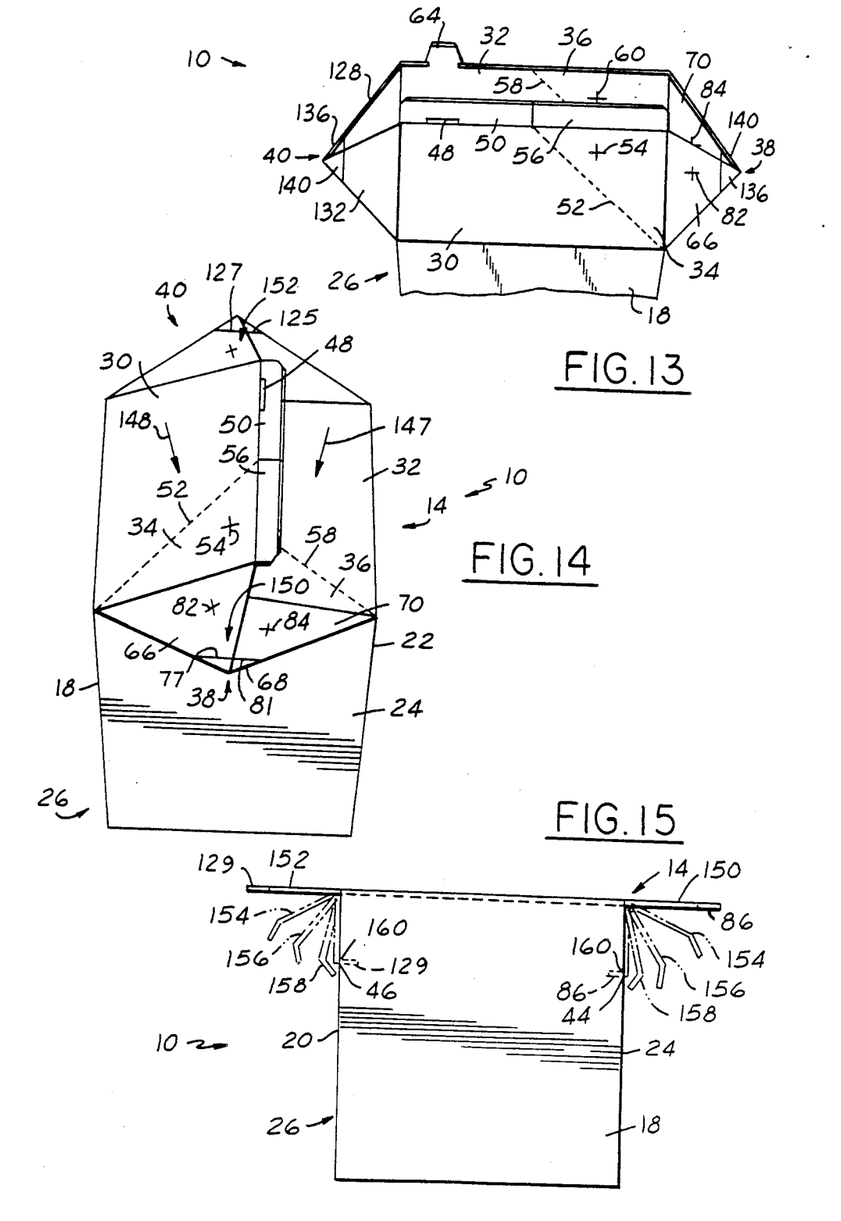
FIG. 13 is a perspective view of the container showing the top portion having its first and second end portions folded inwardly relative to each other as a first step in forming a second storage position.
FIG. 14 is a perspective view of the container showing the top portion foldably formed to produce outwardly protruding flap portions, as a second step in forming the second storage position.
FIG. 15 is a side view of the container showing how the outwardly protruding flap portions are foldably articulated downwardly, as indicated by dashed lines, and how holding portions of the flap portions bend to protrude through slat-type cut-outs in the container to lockably engage with the container.

The infectious waste container 10 is also foldably collapsible into a second storage position for more secure storage and transport of the contents therein. Initially, the top portion 14 should be opened fully, as is best shown in FIG. 6. Referring now to FIG. 13, the next step in forming the top portion 14 into the second storage position involves pulling first and second end portions 38 and 40 respectively outwardly relative to each other to resting positions, as shown in FIG. 13. Referring now to FIG. 14, a downward pressure, as indicated by directional arrow 147, is then applied to second flap portion 32 until second flap portion 32 is laying substantially orthogonal to vertical side panel 22. A like downward pressure 148 is then applied to first flap portion 30 until it too rests in a substantially flush fashion over and against second flap portion 32, and orthogonal to vertical side panel 18. When the first and second flap portions 30 and 32 are then laying substantially orthogonal to side panels 18 and 22, portion 70 will be held in a sandwich-like fashion between portions 66 and 68, and the second end 40 will be folded in a like arrangement, thus forming third and fourth flap portions 150 and 152.

Figure 16:
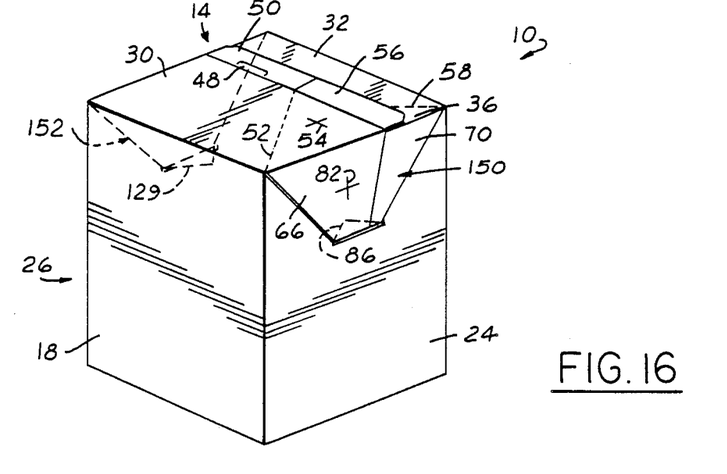
FIG. 16 is a perspective view of the container showing the container in its final assembled second storage position.

Referring now to FIG. 15, the final step of folding the container 10 into its second storage position may be illustrated. To securely seal the container for more prolonged periods of time, and to ensure safe transportation of the container, third and fourth flap portions 150 and 152 may be foldably articualted along partial arcuate paths, as illustrated by phantom lines 154, 156, 158 and 160, until the flap portions 150 and 152 are resting flush against and parallel with vertical side panels 24 and 20 respectively. Along their respective arcuate paths, the holding portion 86 of first end 38 and the holding portion 129 of the second end 40 will also be articulated inwardly relative to each other along folding lines 77 and 81, and 127 and 125 respectively as the flap portions 150 and 152 travel downwardly and inwardly in partial arcuate paths towards each other. The holding sections 86 and 129 will then pass through the slat-type cut-out sections 44 and 46 respectively to a resting position securely inside receptacle means 26. When the third and fourth flap portions 150 and 152 are thus secured as shown in FIG. 15, the container 10 may be more safely transported and its contents stored more securely. The container as it appears in the second storage position is illustrated in FIG. 16.

Figure 17:
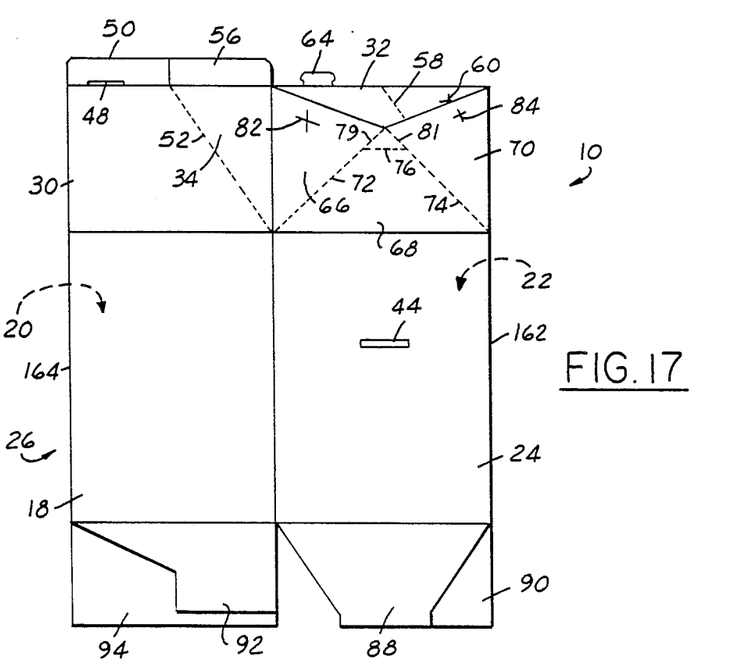
FIG. 17 is a side view of the container showing the container with its top and bottom portions in fully collapsed, or unassembled, positions, thereby forming a substantially flat structure capable of being easily stored before it is used.

In FIG. 17, the container 10 is shown in its fully collapsed state. The container is easily folded into this position by opening the top portion 14 fully as show in FIG. 6, and the bottom portion 16 fully as shown in FIG. 3. Once the top and bottom portions 14 and 16 are opened as shown in FIGS. 6 and 3 respectively, the container may be folded along edge 162, which separates vertical side panels 22 and 24, and edge 164, which separates vertical side panels 18 and 20. The container 10 will then be in a substantially flat position, thereby allowing it to be easily stored until it is ready for use.

The present invention thus serves to provide a lightweight, corrugated infectious waste container capable of being foldably assembled or collapsed. The container further has the added advantages of having a portion of its topside formable into a spout-like configuration for facilitating easier receipt of waste products therethrough, and helping to to prevent accidental human contact with the contents of the container. The container moreover has the advantage of being formable into a first storage position for quick, temporary storage of waste materials, and a second storage position for more permanent storage and safe transportation of the waste materials therein. In addition, the container is relatively easy and inexpensive to manufacture, and due to its inexpensive construction may be discarded along with its contents when it is filled.

Those skilled in the art can now appreciate from the foregoing description that the broad teachings of the present invention can be implemented in a variety of forms. Therefore, while this invention has been described in connection with particular illustrations and examples thereof, the true scope of the invention should not be so limited since other modifications will become apparent to the skilled practitioner upon a study of the drawings, specification and following claims.

What is claimed is:

1. A foldably collapsible container for storing waste in first and second storage positions, said container comprising:

collapsible receptacle means having a foldably sealed bottom portion and a plurality of side panels forming an upwardly opening receptacle for receiving and containing waste therein, said side panels further being integrally formed with said bottom panel; and a top portion integrally formed with said side panels, said top portion being operable to foldably form a spout portion for receiving waste therethrough, said top portion futher being operable to foldably close into said first storage position to thereby facilitate quick closure of said container, and foldably close into said second storage position to facilitate storage of said waste and safe transport of said container.

2. The system of claim 1, wherein said top portion further comprises:
   a plurality of flap portions for helping facilitate foldable closure of said top portion into said first and second storage positions;
   foldably collapsible end portions for further helping to facilitate said foldable closure of said top portion into said first and second storage positions.

3. The system of claim 2, wherein said flap portions further comprise locking means for securely locking said top portion in said first storage position.

4. The system of claim 1, wherein a plurality of said side panels comprise slat portions for further helping to facilitate secure closure of said top portions when said top portion is foldably collapsed into said second storage position.

5. The system of claim 1, further comprising removable, leak-proof liner means adapted to reside within an interior area of said container for further enhancing secure storage of said waste within said container.

6. The system of claim 5, wherein said top portion further comprises a plurality of cut-out portions forming slits for removably receiving portions of said liner means therethrough, said slits thereby operating to help hold and position said liner means securely in place within said container.

7. The system of claim 1, further comprising a removable support member adapted to rest securely on said bottom portion within said container to thereby provide additional structural rigidity to said container.

8. A corrugated, foldably collapsible box-like container for holding and storing infectious and like waste products, said container comprising:
   a foldably collapsible bottom portion;
   a plurality of foldably collapsible vertical side panels integrally formed with said bottom portion to form an upwardly opening box-like receptacle;
   a top portion having first and second foldable flap portions integrally formed with oppositely facing, coplanar side panels and with said end portion, said flap portions being adapted to foldably form a spout portion and further to foldably collapse into first and second storage positions;
   a first end portion adapted to foldably collapse in cooperation with said first and second flap portions into said first and second storage positions, said first end portion being integrally formed with an associated said side panel and with said flap portions, said first end portion further being operable to partially form a spout portion in cooperation with said flap portions to receive therethrough said waste products, said first end portion further being adapted to foldably collapse into said first and second storage positions to help facilitate quick storage of said waste products in said container; and
   a second end portion adapted to foldably collapse in cooperation with said first and second flap portions and said first end portion into said first and second storage position, said second end portion being integrally formed with a side panel facing opposite said side panel associated with said first end.

9. The system of claim 8, wherein said first and second flap portions have score lines adapted to operate cooperatively with said first end portion to help foldably form said spout portion.

10. The system of claim 8, wherein said container further comprises a removable, leak-proof liner adapted to reside within said container for helping to facilitate storage of said waste products without leakage, said liner being removably secured to portions of said flap portions and said first end portion to help hold said liner securely in place.

11. The system of claim 10, wherein said flap portions and said first end portion have a plurality of slit-cuts therethrough for receiving portions of said liner, thereby helping to hold an end portion of said liner securely in an open position within said first end portion when said first end portion is formed into said spout portion.

12. The system of claim 8, wherein a plurality of said panels futher comprise slat-type cut-outs for removably receiving therethrough portions of said first and second end portions to thereby securely hold said container in said second storage position.

13. The system of claim 8, wherein:
   said first storage position is accomplished by applying inwardly directed forces on said first and second end portions relative to each other, thereby causing said first and second end spout portions to fold partially inwardly relative to each other; and
   applying inwardly directed forces to said first and second flap portions relative to each other, whereby said first and second flap portions are foldably articualted to meet and releasably engage each other along their longitudinal edges, thereby forming a triangularly protruding and closed top portion with first and second end portions sloping inwardly relative to each other in a partially foldably collapsed fashion.

14. The system of claim 8, wherein said second storage position is accomplished by:
   applying outwardly directed forces on said first and second end portions relative to each other, thereby, causing said first and second end portions to move outwardly relative to each other into resting, outwardly protruding positions;
   applying inwardly directed forces on said first and second flap portions relative to each other, whereby said first and second flap portions and said first and second end portions foldably collapse in an overlapping fashion to form a substantially longitudinally flush top portion, having third and fourth flap portions extending longitudinally outward from said container;
   folding said third and fourth flap portions inwardly relative to each other and downward relative to said first and second flap portions; and
   folding inwardly a holding portion of said first end portion and a holding portion of said second end portion and releasably engaging said holding portions in associated slat-type cut-outs disposed in said side panels to hold said third and fourth flap portions substantially flush with said side panels.

15. The system of claim 8, whereby said first end portion has a holding portion operable to move with a snap-action like force into an inwardly resting position, thereby helping to hold said first end portion open when said first end portion is formed into said spout portion.

16. The system of claim 8, wherein said vertical side panels, said bottom portion and said top portion are foldably collapsible to form a substantially flat structure to facilitate storage of said container before said container is used.

17. A foldably collapsible waste container adapted to collapse into first and second storage positions, said container comprising:
   box-type receptacle means opening upwardly for holding said waste;
   a top portion having first and second flap portions and first and second end portions integrally formed with said receptacle means, said first end portion and portions of said first and second flap portions being adapted to foldably form a spout-like opening for receiving therethrough waste products and directing said waste products into said receptacle means;
   said first and second end portions further being operable to fold partially inward relative to each other, whereby partial inward folding of said first and second end portions operates to pull longitudinal edges of said first and second flap portions toward each other and into abutting contact, thereby forming said first storage position; and
   said first and second end portions further being operable to fold outward relative to each other, whereby outward folding of said first and second end portions operates to pull said first and second flap portions into overlapping and substantially longitudinally flush contact with each other, thereby forming third and fourth flap portions said third and fourth flap portions further being operable to foldably collapse into positions parallel with portions of said receptacle means and matingly engage with said receptacle means, thereby forming said second storage position.

18. The system of claim 17, wherein said first and second flap portions further comprise score lines for allowing portions of said first and second flap portions to fold outwardly relative to each other when said first end is formed into said spout, said portions of said first and second flap portions thereby operating cooperatively with said first end portion to help form said spout-like opening.

19. The container of claim 17, further comprising removable, leak-resistant liner means adapted to rest nestably within said receptacle means and line interior areas of said first and second flap portions and said first end portion when said first end portion and said first and second flap portions are formed into said spout-like opening.

20. The container of claim 19, wherein said liner means is a leak-resistant plastic bag removably disposed within said receptacle means.

21. The container of claim 20, wherein said first end portion and said first and second flap portions have slit-cuts for receiving therethrough portions of said plastic bag and holding said plastic bag securely in an open position.

22. The system of claim 17, wherein said first end further comprises a plurality of score lines forming a triangular holding section, said triangular holding section being operable to move with a snap-like force into an inward resting position relative to said second end portion to help hold said first end portion in a spout-like opening.

23. The system of claim 17, wherein said second flap portion further comprises a locking tab element protruding therefrom operable to fold along a longitudinal portion of said second flap portion; and
   wherein said first flap portion further comprises a slat-type cut-out portion for removably receiving therethrough said locking tab element when said frist and second flap portions are foldably collapsed in said overlapping and substantially flush contact, said locking tab element and said slat-type cut-out portion thereby operating cooperatively to secure said first and second flap portions in said overlapping and substantially flush contact.

24. The system of claim 17, wherein said receptacle means has a plurality of vertical sections, said first and second end portions each being associated with particular vertical sections having slat-type cut-out portions therein, said slat-type cut-out portions being operable to receive therethrough portions of said first and second end portions, thereby holding said first and second end portions securely parallel and in abutting contact with said particular vertical sections, and thereby helping form a sealed box-type structure when said container is in said second storage position.

25. The container of claim 17, wherein interior areas of said receptacle means, said first and second end portions and said first and second flap portions are all coated with a moisture resistant coating.

26. The container of claim 25, wherein said moisture resistant coating is a thin wax coating.

27. The system of claim 17, further comprising a removable panel member adapted to rest nestably within said receptacle means and operable to provide additional structural support to said receptacle means.

* * * * *

UNITED STATES PATENT AND TRADEMARK OFFICE
CERTIFICATE OF CORRECTION

PATENT NO. : 4,969,596
DATED : November 13, 1990
INVENTOR(S) : Robert I. Schulbaum It is certified that error appears in the above-identified patent and that said Letters Patent is hereby corrected as shown below:

Column 7, line 42;   "connector" should be --container--.

Column 8, line 31;   "show" should be --shown--.

Column 10, line 6;   "position" should be --positions--.

Column 12, line 28;  "frist" should be --first--.

Signed and Sealed this

Fourteenth Day of July, 1992

Attest:

DOUGLAS B. COMER

Attesting Officer    Acting Commissioner of Patents and Trademarks